United States Patent [19]

Ahlstrand

[11] Patent Number: 4,706,340
[45] Date of Patent: Nov. 17, 1987

[54] METHOD AND AN ARRANGEMENT FOR PRODUCING A FIBRE LAYER

[75] Inventor: Ove Ahlstrand, Älvsjö, Sweden

[73] Assignee: Mo och Domsjo AB, Sweden

[21] Appl. No.: 868,376

[22] Filed: May 29, 1986

[30] Foreign Application Priority Data

Jul. 2, 1985 [SE] Sweden ............................ 8503292

[51] Int. Cl.[4] ........................... B01D 9/00; C01F 5/34
[52] U.S. Cl. ........................................ 19/296; 19/304; 19/305
[58] Field of Search ................ 19/296, 303, 304, 305, 19/148, 301, 88, 89; 264/518

[56] References Cited

U.S. PATENT DOCUMENTS

| | | | |
|---|---|---|---|
| 2,116,663 | 5/1938 | Powell | 19/304 X |
| 2,195,158 | 3/1940 | Watts | 19/304 |
| 2,715,755 | 8/1955 | Jones | 19/304 X |
| 2,729,861 | 1/1956 | Downey | 19/304 |
| 2,953,187 | 9/1960 | Francis, Jr. | 19/305 X |
| 3,332,114 | 7/1967 | Oja | 19/305 X |
| 3,396,433 | 8/1968 | Roxlo | 19/304 |
| 4,494,278 | 1/1985 | Kryer | 19/304 |

Primary Examiner—Louis K. Rimrodt
Assistant Examiner—J. L. Olds
Attorney, Agent, or Firm—Sughrue, Mion, Zinn, Macpeak, and Seas

[57] ABSTRACT

When practicing a method and using an arrangement for producing a fibre layer or fibre mat from a liquid-absorbent material, e.g. in the manufacture of diapers, a fibre-air suspension is blown in between two endless, mutually parallel air-permeable conveyor belts (12,13) at a pressure which exceeds the pressure of the ambient surroundings. The conveyor belts form therebetween a forming space which is defined laterally by stationary or movable side-walls (18), the inner surfaces of which may be profiled so as to provide a fibre layer or a fibre mat with profiled side-edges.

7 Claims, 5 Drawing Figures

METHOD AND AN ARRANGEMENT FOR PRODUCING A FIBRE LAYER

The present invention relates to a method of producing a uniform layer of fibre, in which method a fibre-air suspension is fed into a forming space located between two air-permeable conveyer belts which move in mutually the same direction, and in which there is established between the forming space and the ambient surroundings a pressure difference which results in the deposition of fibres onto the mutually facing surfaces of respective belts. The invention also relates to an arrangement for carrying out the method. By fibres is meant here and in the following primarily cellulose fibres, such as fluff, although the invention can also be applied with fibres other than cellulose fibres.

It is well known to form fibre layers, or fibre mats, for use in the manufacture of liquid absorbent pads for diapers, incontinence guards and the like, by drawing a fibre-air suspension by suction in between two wires or like air-permeable conveyer belts. As illustrated for example in U.S. patent specification No. 3,332,114, the suction effect is obtained through the agency of suction boxes which surround the wires and which create a partial vacuum on the respective outer surfaces thereof. The fibres, which comprise, for example, cellulose fibres and which are drawn by suction into the space between the mutually facing surfaces of the two wires, are deposited on the wires in the proximity of the suction area One serious drawback with layer forming methods of this kind is that the two fibre layers, which are compressed to form a single layer through, for example, mutual convergence of the two wires towards the outlet end, obtain mutually different densities, and in certain instances, exhibit significant irregularities. The reason for this is because subsequent to that part of respective wires lying nearest the inlet end being quickly coated with fibre, the suction effect exerted on the fibres becomes negligible, so that fibres suspended in the air are slowed-down and fall onto the bottom wire, to form an excessively thick fibre layer thereon. There is also the risk that fibres will drop from the upper wire, subsequent to the build-up of suction due to a thick fibre layer.

These irregularities and variations in density have made it necessary to overdimension the nominal thickness of the fibre mat by increasing the suction effect, in order to ensure that the finished product, e.g. a sanitary napkin, has across the whole of the liquid absorbing surface thereof a thickness of such magnitude as to eliminate the possibility of liquid seeping from or penetrating the product. This overdimensioning of the thickness of the product naturally results in higher manufacturing costs.

It is therefore a main object of the invention to provide a novel method of producing a fibre layer or a fibre mat which will enable a layer of uniform thickness and fully controllable density to be obtained and which also results in reduced fibre consumption.

A further object of the invention is to provide an arrangement for practising the method and for enabling the production of fibre mats or webs whose side-edges are profiled in a desired configuration.

These objects are fully realized with the method and the arrangement defined in the following claims.

The invention will now be described in more detail with reference to the accompanying drawings, in which FIG. 1 is a central, vertical sectional view of an arrangement according to the invention;

Figure 1:
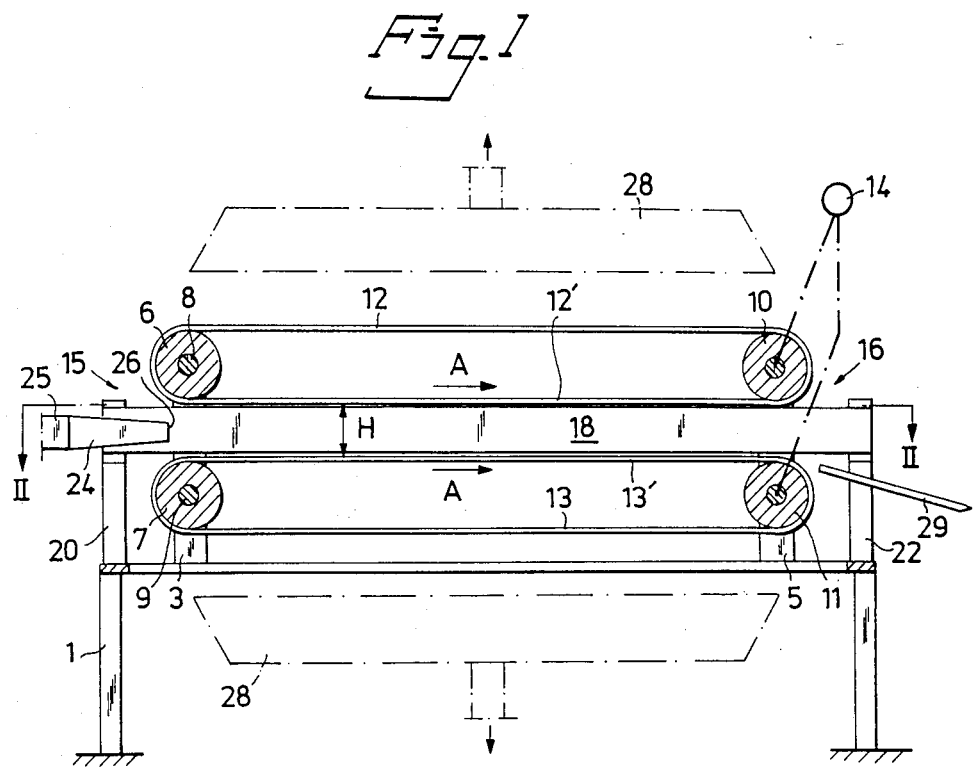
Figure 2:
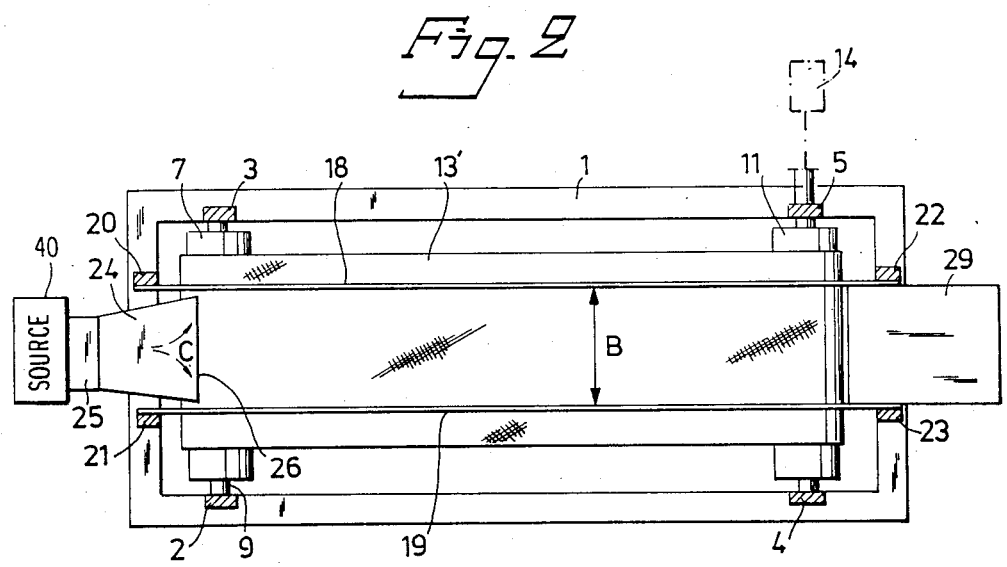
FIG. 2 is a sectional view taken on the line II—II in FIG. 1.
Figure 4:
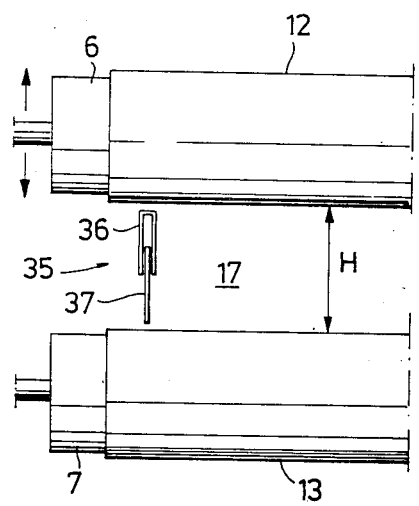
FIG. 4 is a simplified view of the two conveyor belts, and illustrates schematically a telescopic side-wall.
Figure 5:
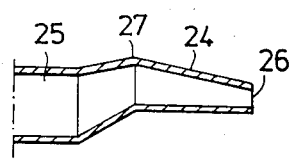
FIG. 5 is a simplified view of a distribution nozzle.

The arrangement illustrated in FIGS. 1 and 2 comprises a frame structure 1 which supports two pairs of mutually spaced bracket structures 2,3 and 4,5. The one pair of bracket structures 2,3 supports the respective shafts 8 and 9 of two rotatably mounted cylindrical rolls 6 and 7 arranged one above the other in mutually spaced relationship, while two further cylindrical rolls 10 and 11 are mounted for rotation in a similar manner in respective bracket structures 4 and 5. Extending around the rolls 6 and 10 is a first endless air-permeable conveyor belt 12, for example a wire, while a second air-permeable conveyor belt 13 extends around the other rolls 9 and 11. The mutually facing belt sections 12' and 13' of the two conveyor belts 12 and 13 extend parallel with one another, i.e. when the rolls 6,7,10,11 used in the arrangement have mutually the same diameter, the distance between the shafts 8 and 9 is equal to the distance between the shafts 10 and 11. Although it is preferred to use rolls of mutually the same diameter, it is also possible to use, for example, a first diameter in respect of the roll pairs 6, 7 and a second diameter in respect of roll pair 10,11. It is important, however, that the space between the belt sections 12' and 13' has the same height H along the whole length of the space. In the illustrated embodiment the two rolls 10 and 11 are driven synchronously by a motor 14, preferably an electric motor, so that the two preferably horizontal belt sections 12' and 13' which define the forming space vertically move, in the direction of the arrows A, with the same speed from a fibre-air suspension inlet 15 to an outlet 16. The forming space, designated 17 in FIG. 4, is defined laterally by side-walls 18 and 19 arranged between the belt sections 12' and 13'. In the embodiment illustrated in FIGS. 1 and 2 the side-walls comprise, for example, polished stainless steel plate, plastic sheets or the like, and are impervious to air. The upper and lower edges of the side-walls lie in abutment with or are closely adjacent to respective belt sections 12' and 13', in order to achieve the best possible sealing effect. In the illustrated embodiment the side-walls 18 and 19 are stationary and are attached at the ends thereof to respective vertical bracket structures 20,21,22 and 23. Arranged at the inlet 15 is a nozzle 24 having a broad nozzle orifice 26, the width of which is preferably equal to the width B of the forming space, corresponding to the lateral distance between the two mutually parallel side-walls 18 and 19, so as to obtain the best possible distribution of fibre suspension blown into the forming space 17. This fibre suspension is supplied to the nozzle 24 from a source 40 through a pipe or conduit 25, and the pressure in the suspension is higher than the ambient surrounding pressure, which is normally equal to atmospheric pressure. In order to obtain the best possible lateral spread of fibres during their passage to the broad nozzle orifice 26 of the nozzle 24, the nozzle is suitably provided with at least one angled part or knee 27 (cf. FIG. 5) operative in causing the flow of suspension to slow down and in forcing the fibres to spread laterally, as indicated by the arrow C in FIG. 2.

In FIG. 1 there is shown in broken lines two suction devices 28 intended for removing dust by suction. More specifically, the sole purpose of these devices is to withdraw air which flows outwardly from the wires or conveyor belts and which may possibly contain fibres, these devices having a totally negligible effect on the pressure in the surrounding area.

Figure 3:
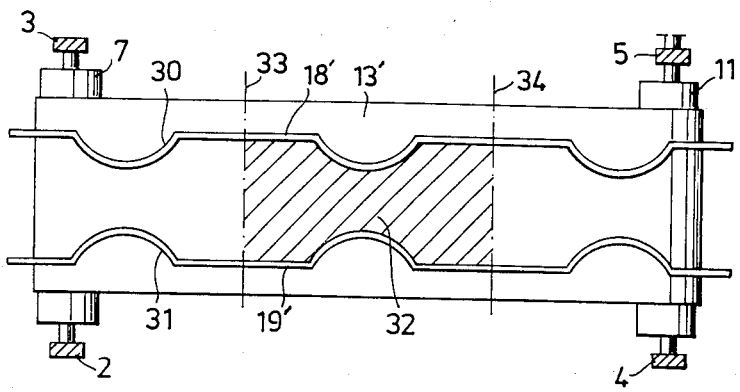
FIG. 3 illustrates the lower conveyor belt, provided with profiled side-walls.

Fibres, e.g. cellulose fibres, suspended in gas, preferably air, are blown into the inlet 15 and into the forming space 17 by means of the nozzle 24 at a suitable overpressure, for example a pressure of 600-700 mm water column, wc. Initially the outlet is blocked momentarily, in order to enable a fibre "plug" to form. This plug is required in order to prevent the fibre-air suspension, which may be injected into the forming space, for example, at a velocity of 20-25 m/s, from passing straight through the forming space, and forms in the forming space 17 an area of high fibre density, and is constantly renewed with fresh fibres as fibres as deposited on the conveyor belts as a result of the higher pressure which prevails in the forming space relative to the ambient surrounding. Because of the inherent velocity and overpressure of the fibre suspension, the deposition of fibres is controlled totally by the density of the fibre layers formed on respective belt sections 12' and 13', and when the conveyor belts 12 and 13 are set to travel at a suitable speed there is no risk of particles or fibres being slowed down and deposited on regions of dense fibre layers. When applying this principle there is obtained, quite surprisingly, an extremely uniform fibre mat. The two fibre layers thus formed depart from the outlet 16 in the form of a single layer, which in the embodiments illustrated in FIGS. 2 and 3 is assumed to slide down on an inclined slide plate 29 or on a belt conveyor for transportation to a diaper manufacturing machine (not shown).

The fibre mat produced in the arrangement according to FIGS. 1 and 2 have smooth mutually parallel side-edges formed by the two planar and mutually parallel side-walls 18,19. It is also possible, however, when practising the invention to produce a fibre mat or a fibre layer having the configuration illustrated in FIG. 3, which shows the wire section 13' of the lower wire 13 facing towards the forming space 17. Firmly mounted around the whole parameter of the wire are profiled endless side-walls made of a flexible material, such as rubber for example. The side-walls are so profiled with inwardly directed bulges 30,31 that the mutually opposite side-edges of the formed fibre mat are similarly recessed to form narrow or necked portions 32 at given locations along the side-edges. Thus, when a formed fibre mat is clipped or similarly cut along the lines 33 and 34, there is obtained an absorbent body for incorporation in a disposable diaper for example, this absorbent body being illustrated by the hatched area of the fibre mat shown in FIG. 3. It will be understood that the profiled walls may also be passed around separate rolls, of which some are driven, and the axes of rotation of which lie at right angles to the axes of rotation of the drive rolls 6,7,10,11. Alternatively, the side-walls can be moved with the aid of other suitable means.

In certain instances an advantage is gained when the vertical height of the forming space 17 can be adjusted, by moving the rolls of respective roll pairs towards or away from one another. To this end, the rolls 6 and 10 may be mounted in their respective bracket structures 2,3 and 4,5 so as to be vertically displaceable therein. Since the height of each side-wall 18,19 corresponds to the height H of the forming space 17, it must also be possible, in this latter case, to adjust the height of sidewalls. As shown by the simplified illustration in FIG. 4, this can be readily achieved by making each side-wall telescopic. The detail illustration of FIG. 4 shows the left endpart part of the two rolls 6,7 and a modified side-wall 35, corresponding to the side-wall 18 in FIG. 1, seen from the inlet 15. The side-wall 35 is divided into a first upper wall-part 36 in the form of a twin-plate into which a lower wall-part 37 can be inserted, the ends of the two wall-parts 36,37 being displaceably mounted in, for example, the bracket structures 20 and 22 in FIG. 1.

Although the invention has been described in the aforegoing with reference to a number of embodiments thereof, it will be understood that the various components of the arrangement can be exchanged for other components of a kind known per se, without departing from the concept of the invention. It is also possible to provide further roll pairs, for supporting the conveyor belt or for providing support rolls between the illustrated roll pairs.

The method and arrangement according to the invention provide an extremely uniform layer, thereby rendering it unnecessary to overdimension the thickness of the layer. In addition, a great saving in energy is achieved since the necessary overpressure can be obtained at a far lower cost than in the case of corresponding arrangements requiring a vacuum.

The inner overpressure of the forming space 17 in relation to the pressure of the air surrounding the forming space can be readily varied by adjusting, for example, the velocity at which the fibre suspension is blown in the forming space.

I claim:

1. A method for producing a uniform fibre layer, comprising the steps of defining a forming space between two air-permeable conveyor belts arranged for movement in mutually the same direction, introducing a fibre-air suspension into the forming space, and maintaining between the forming space and the ambient surroundings a pressure difference such as to cause the deposit of fibres on mutually facing surfaces of the conveyor belts, said defining step including the steps of arranging mutually facing belt sections (12',13') of the conveyor belts parallel with one another and arranging between said surfaces substantially sealing side-walls (18,19); said maintaining step including the step of blowing the fibre-air suspension into the forming space at a pressure sufficient to create within said forming space a pressure which exceeds the pressure of the ambient surroundings.

2. A method according to claim 1, characterized by blowing the fibre-air suspension into the forming space with the aid of a nozzle (24) having a nozzle width substantially equal to the width (B) of the forming space (17).

3. An arrangement according to claim 1, characterized in that the surfaces of the side-walls facing the forming space (17) are profiled with regularly spaced, inwardly directed bulges (30,31).

4. An arrangement for producing a uniform fibre layer, including two conveyor belts (12,13); a plurality of rolls (6,7,10,11) for driving said conveyor belts in the same direction and for defining a forming space therebetween; and means for establishing between the forming space and the ambient surroudings a pressure difference such as to cause fibres to be deposited on the mutually facing and mutually parallel surfaces of the conveyor belts, said arrangement further including two mutually parallel and substantially sealing side-walls (18,19) positioned between mutually facing belt sections (12',13') of the conveyor belts to define the forming space (17) laterally; a nozzle (24,26) adapted to introduce the fibre-air suspension into the forming space; and a source (40) for supplying the fibre-air suspension into the forming space at a pressure sufficient to create in the forming space a pressure which exceeds the pressure in the ambient surroundings around the forming space.

5. An arrangement according to claim 4, characterized in that the side-walls (18,19) are stationary.

6. An arrangement according to claim 4, characterized in that an exit orifice (26) of the nozzle (24) has a width which corresponds essentially to the width (B) of the forming space.

7. An arrangement according to claim 4, characterized in that at least one conveyor belt (12) is supported by rolls (6,10) which can be adjusted vertically.

* * * * *